United States Patent [19]

Weiguny et al.

[11] Patent Number: 5,719,284

[45] Date of Patent: Feb. 17, 1998

[54] PROCESS FOR THE PREPARATION OF SUBSTITUTED 3-ARYLQUINAZOLINE-2,4-DIONES

[75] Inventors: Jens Weiguny, Weiterstadt; Holger Borchert, Frankfurt; Thomas Gerdau, Eppstein, all of Germany

[73] Assignee: Hoecht Aktiengesellschaft, Germany

[21] Appl. No.: 646,678

[22] Filed: May 10, 1996

[30] Foreign Application Priority Data

May 10, 1995 [DE] Germany ............... 195 170 35.0
Jun. 10, 1995 [DE] Germany ............... 195 170 36.9

[51] Int. Cl.$^6$ ............................................. C07D 239/96
[52] U.S. Cl. .......................................... 544/285; 514/259
[58] Field of Search ............................................. 544/285

[56] References Cited

U.S. PATENT DOCUMENTS

| | | | |
|---|---|---|---|
| 4,405,623 | 9/1983 | Ishikawa et al. | 424/251 |
| 4,634,769 | 1/1987 | Bandurco et al. | 544/285 |
| 4,639,518 | 1/1987 | Bandurco et al. | 544/285 |
| 5,539,114 | 7/1996 | Cosmo et al. | 544/285 |

FOREIGN PATENT DOCUMENTS

| | | |
|---|---|---|
| 894239 | 2/1972 | Canada. |
| 0 040 793 | 12/1981 | European Pat. Off.. |
| 360417 | 3/1990 | European Pat. Off.. |
| 1804391 | 5/1970 | Germany. |
| 1059271 | 2/1967 | United Kingdom. |

OTHER PUBLICATIONS

E. P. Papadopoulos and C.D. Torres, *Convenient Preparation of N–Substituted 2–Amino–4H–3, 1–Benzoxazin–4–ones and 3–Substituted 2,4(H, 3H)–Quinazolinediones*, J. Heterocylc. Chem 19:269–272, (1982).

Enzo Alessio and Giovanni Mestroni, *Catalytic Reductive Carbonylation of Aromatic Nitro Compounds to Urethanes Promoted by Supported Palladium Activated with, 1,10–Phenanthroline Derivatives*, J. Organomet. Chem. 291:117–127 (1985).

S. Cenine, S. Console, C. Crotti and S. Tollari, *Metal Catalyzed Deoxygenation by Carbon Monoxide of o–substituted Nitrobenzenes, Synthesis of 1,4–dihydro–2H–3, 1–benzoxazin–2–one derivatives*, J. Organomet. Chem. 451:157–162 (1993).

C. V. Rode, S. P. Gupte, R. V. Chaudhari, C. D. Pirozhkov, A. L. Lapidus, *Activity and Selectivity of Supported Rh Complex Catalyst in Carbonylation of Nitrobenzene*, J. Mol. Catal. 94:195–206 (1994).

Organic Preparation and Procedures Int. 10:13–16 (1978).

Primary Examiner—Matthew V. Grumbling
Attorney, Agent, or Firm—Connolly & Hutz

[57] ABSTRACT

The invention relates to a process for the preparation of substituted 3-arylquinazoline-2,4-diones of the formula (I)

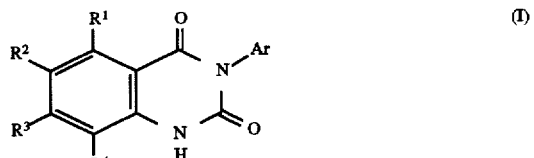

in which $R^1$, $R^2$, $R^3$ and $R^4$ are as defined in claim 1 and Ar is

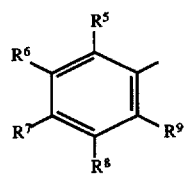

where $R^5$ to $R^9$ are as defined in claim 1, by reacting a compound of the formula (II)

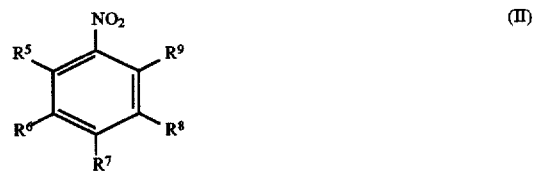

with a compound Z in the presence of a catalyst, a ligand and a solvent, where Z is a) an anthranilic acid derivative of the formula (III)

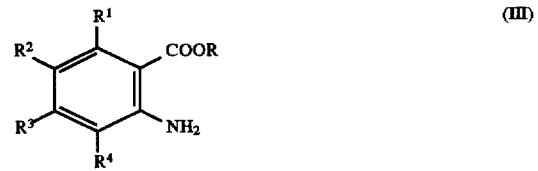

or b) an alcohol $R^{10}$—OH and where, in case b), the resulting carbamate is then reacted with an anthranilic acid derivative of the formula III.

15 Claims, No Drawings

PROCESS FOR THE PREPARATION OF SUBSTITUTED 3-ARYLQUINAZOLINE-2,4-DIONES

Substituted 3-arylquinazoline-2,4-diones of the formula (I) are interesting intermediates for pharmaceuticals and plant protection agents (U.S. Pat. No. 4,405,623; GB 1,059,271; EP 360,417).

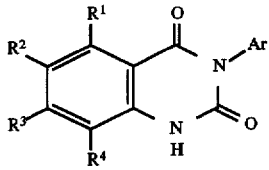
(I)

(I) is customarily prepared by reaction of anthranilic acid or of an alkyl anthranilate with an aryl isocyanate in a reaction medium which is inert to isocyanates.

In the case of anthranilic acids, N-arylcarbamoylanthranilic acids are thus obtained, which are intermediately isolated, optionally purified by recrystallization and then ring-closed in a second reaction step, e.g. in polyphosphoric acid in the course of 5 hours at 150° C. (EP 360,417) or a protic organic medium, such as ethanol in the presence of excess, strong mineral acid, preferably gaseous hydrochloric acid, to give 3-arylquinazoline-2,4-diones of the formula (I) (GB 1,059,271, Ex. 3). In a corresponding manner, the alkyl anthranilates on reaction with aryl isocyanates yield alkyl N-arylcarbamoylanthranilates, which are intermediately isolated and can be cyclized in a similar manner to the acids to give the 3-arylquinazoline-2,4-diones. It is also known to carry out the cyclization to give (I) in protic media such as ethanol or methanol in the presence of aqueous sodium hydroxide (German Offenlegungsschrift 1,804,391, Ex.4; J. Heterocycl. Chem. 19 (2), p. 269, 1982).

The aryl isocyanates are in general prepared by phosgenation of the corresponding anilines (Houben Weyl, Volume E4, p. 741), which in turn can be obtained from the corresponding nitroaromatics by reduction (Houben Weyl, Volume 11/1, p. 360).

The use of highly toxic phosgene and thus that of chlorine, which does not appear in the final product, makes this two-stage process additionally expensive and is associated with problems with respect to environmental protection and safety.

Altogether, the synthesis of (I) starting from the corresponding nitroaromatics proceeds in 4 stages and comprises the use of toxic phosgene and isocyanates. There was therefore a need to develop a shorter, improved process for the preparation of 3-arylquinazoline-2,4-diones.

This object is achieved by a process for the preparation of substituted 3-arylquinazoline-2,4-diones of the formula (I)

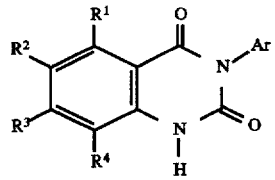
(I)

in which $R^1$, $R^2$, $R^3$ and $R^4$ independently of one another are hydrogen, halogen, $(C_1-C_{12})$alkyl, $(C_1-C_{12})$alkoxy, Ar or ArO and Ar is

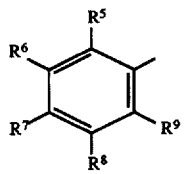

where $R^5$ to $R^9$ independently of one another are hydrogen, halogen, $(C_1-C_{12})$alkyl, $(C_1-C_{12})$alkoxy, phenyl or phenoxy, it being possible for $R^5$ and $R^6$, $R^6$ and $R^7$, $R^7$ and $R^8$ or $R^8$ and $R^9$ also to form a further aromatic ring, which comprises reacting a compound of the formula (II)

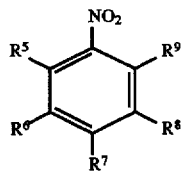
(II)

in which $R^5$ to $R^9$ have the abovementioned meaning, with carbon monoxide and a compound Z in the presence of a catalyst, a ligand and a solvent, where Z is a) an anthranilic acid derivative of the formula (III)

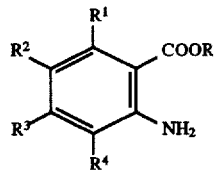
(III)

where $R^1$ to $R^4$ have the abovementioned meaning and R is hydrogen or $(C_1-C_{12})$alkyl, or b) an alcohol of the formula (IV)

$$R^{10}\text{—OH} \quad (IV)$$

where $R^{10}$ is $(C_1-C_{12})$alkyl and where, in case b), the resulting carbamate of the formula (V)

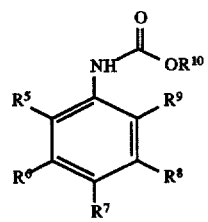
(V)

is then reacted with an anthranilic acid derivative of the formula (III) in the presence of a base and of an aprotic solvent.

The process according to the invention is important for the preparation of compounds of the formula (I) in which $R^1$ to $R^9$ are hydrogen, halogen, $(C_1-C_6)$alkyl or $(C_1-C_6)$alkoxy, in particular for the preparation of 3-(2,4-dichlorophenyl)-6-fluoro-2,4-(1H, 3H)-quinazolinedione.

The reductive carbonylation is carried out in the presence of noble metals of the 8th subgroup, preferably in the presence of Pd (J. Organomet. Chem. 291, 117–27, 1985), Ru (J. Organomet. Chem. 451, 157–62, 1993) and Rh (J. Mol. Catal. 94, 195–206, 1994) and ligands such as pyridine, tert-amines or phosphines and their derivatives, bidentate ligands, such as, for example, bipyridine or phenanthroline derivatives, being preferred. Phosphines which can be employed are, for example, bisdiphenylphosphinomethane, bisdiphenylphosphinoethane, bisdiphenylphosphinopropane, bisdiphenylphosphinobutane or Naphos. The noble metals can be present in the form of their salts, such as the halides, acetates, sulfates etc., their oxides or in the form of complexes, such as the carbonyl complexes. It is also possible to employ the catalyst in metallic form on an inert support such as active carbon or alumina.

In many cases, it has proven useful to employ a catalyst which consists of one of the metal compounds mentioned and a Lewis or Brönstedt acid. The acid employed can be, for example, p-toluenesulfonic acid, substituted benzoic acids, such as 2,4,6-trimethylbenzoic acid, or pivalic acid. It has proven favorable to employ 0.001 to 10 mol %, in particular 0.01 to 1 mol %, of catalyst relative to nitro groups in the solution. For ligand and acid, the expedient amount is in the range from 0.1 to 100-fold the amount of catalyst employed, but does not have to be identical.

The reaction of the compound of the formula (II) with a compound Z is carried out at temperatures of 75°–250° C., in particular of 100°–180° C., and CO pressures of 20 to 500 bar, in particular 50 to 200 bar. The reaction proceeds in aprotic reaction media, e.g. aromatic, aliphatic or cycloaliphatic hydrocarbons, which can have inert substituents, e.g. alkyl or chloro substituents, heterocycles or ketones, in particular mononuclear alkylaromatics, or alkanes and cycloalkanes which are liquid under normal conditions. In many cases, toluene, xylene and dichlorobenzene in pure form or as an isomer mixture have proven suitable.

In the case where Z is an alcohol of the formula (IV), however, it is expedient also to use this alcohol as a solvent. In this case, it can also be diluted by inert solvents, e.g. xylene, toluene or dichlorobenzene.

In the case of the reaction of a compound of the formula II with an anthranilic acid derivative of the formula III, both reaction components can be initially introduced together, however, it is also possible to meter in the anthranilic acid derivative during the reaction. It has proven expedient to employ the compounds (II) and (III) in a molar ratio from 0.9:1 to 1.1:1.

In the case where a compound of the formula II is reacted with an alcohol of the formula IV, the carbamates of the formula (V) obtained are then cyclized with the anthranilic acid derivatives of the formula (III) in the presence of a base and of an aprotic solvent. In this context, it has proven useful to employ the compounds (V) and (III) in the molar ratio from 0.9:1 to 1.1:1. It has proven favorable to use, as base, alkali metal or alkaline earth metal alkoxides, amides or hydrides or tetraalkylammonium hydroxides. The aprotic solvent employed can be, for example, an aromatic, aliphatic or cycloaliphatic hydrocarbon which can also carry inert substituents such as alkyl or chloro substituents. Heterocycles or ketones also yield good results as solvents, if they are inert to the base. In many cases toluene, xylene or dichlorobenzene have proven suitable in pure form or as an isomer mixture.

The alkali metals or alkaline earth metal alkoxides, amides or hydrides used as a base can be employed in solid form or as a solution in the corresponding alcohols. In many cases, the use of sodium methoxide in methanol has proven suitable. If alkali metal or alkaline earth metal hydrides or amides are used, these can also be employed in solid form or as a suspension in an inert solvent. The bases used are customarily employed in amounts of 0.5 to 95 mol % based on the starting materials. It has proven favorable to use amounts of 1 to 20 mol %, in particular 5 to 10 mol %. The reaction temperature of the cyclization is expediently selected such that the alcohol liberated from the reaction medium is distilled off. Preferably, the temperatures are between 100° and 200° C.

The smooth course and the high yield of the cyclization step were particularly surprising, as in the reaction of N-phenylalkylcarbamates with anthranilic acid (Organic Preparations and Procedures Int. 10(1), 13–16, 1978) only a moderate yield of at best 60% is described if anthranilic acid is heated to 180° C. with alkyl N-phenylcarbamates. In addition, the carbamate had to be added in an excess.

EXAMPLE 1 a) Reductive carbonylation of 2,4-dichloronitrobenzene: 22.4% by weight of 2,4-dichloronitrobenzene, 2.0% by weight of Pd—C (5%), 1.3% by weight of 2,4,6-trimethylbenzoic acid and 0.4% by weight of 3,4,7,8-tetramethyl-1,10-phenanthroline are dissolved in 73.8% by weight of methanol and filled into an HC-4 autoclave. A pressure of 100 bar of CO is set and the temperature is increased to 180° C. After 2 hours, the experiment is terminated and the solution is investigated by gas chromatography. The conversion was 100% at a selectivity for the methyl N-2,4-dichlorophenylcarbamate of 85%.

b) Preparation of 3-(2,4-dichlorophenyl)-6-fluoro-2,4 (1H,3H)-quinazolinedione: 8.5% by weight of N-2,4-dichlorophenylcarbamate, 6.5% by weight of methyl 5-fluoroanthranilate and 0.1% by weight of sodium methoxide are dissolved in 84.9% by weight of o-dichlorobenzene and heated to 170° C. The methanol formed is distilled off during the course of this. The precipitate formed is separated off and a 91.3% yield of 3-(2,4-dichlorophenyl)-6-fluoro-2,4(1H,3H) quinazolinedione is thus obtained.

EXAMPLE 2

Preparation of 3-(2,4-dichlorophenyl)-6-fluoro-2,4 (1H,-3H)-quinazolinedione:

17.2% by weight of 2,4-dichloronitrobenzene, 15.6% by weight of methyl 5-fluoroanthranilate, 1.5% by weight of Pd—C (5%), 1.0% by weight of 2,4,6-trimethylbenzoic acid and 0.4% by weight of 3,4,7,8-tetramethyl-1,10-phenanthroline are dissolved in 64.3% by weight of toluene and filled into an HC-4 autoclave. A pressure of 100 bar of CO is set and the temperature is increased to 180° C. After 2 hours, the autoclave is allowed to cool, and the product is filtered off together with the active carbon and recrystallized from dichlorobenzene. 51% of 3-(2,4-dichlorophenyl)-6-fluoro-2,4(1H,3H)-quinazolinedione is obtained.

We claim:

1. A process for the preparation of a substituted 3-arylquinazoline-2,4-dione of the formula (I)

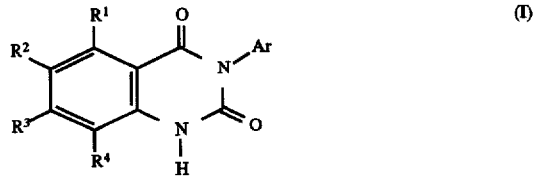

in which $R^1$, $R^2$, $R^3$ and $R^4$ independently of one another are hydrogen, halogen, $(C_1–C_{12})$alkyl, $(C_1–C_{12})$alkoxy, Ar or ArO and Ar is

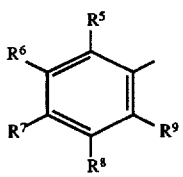

where $R^5$ to $R^9$ independently of one another are hydrogen, halogen, $(C_1-C_{12})$alkyl, $(C_1-C_{12})$alkoxy, phenyl or phenoxy, or $R^5$ and $R^6$, $R^6$ and $R^7$, $R^7$ and $R^8$ and $R^9$ can form a further aromatic ring, which comprises reacting a compound of the formula (II)

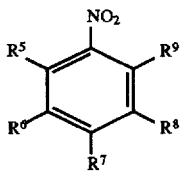

(II)

with carbon monoxide and a compound Z in the presence of (a) a reductive carbonylation catalyst which is a noble metal or a compound or complex thereof, alone or in combination with a Lewis or Brönsted acid, (b) an amine or phosphine ligand and (c) a reaction medium, where Z is a) an anthranilic acid derivative of the formula (III)

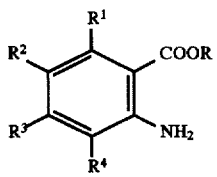

(III)

where $R^1$ to $R^4$ have the abovementioned meaning and R is hydrogen or $(C_1-C_{12})$alkyl, or b) an alcohol of the formula (IV)

 $R^{10}$—OH (IV)

where $R^{10}$ is $(C_1-C_{12})$alkyl and where, in case b), the resulting carbamate of the formula (V)

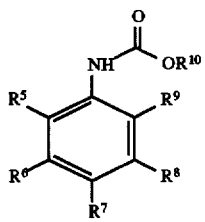

(V)

is then reacted with an anthranilic acid derivative of the formula (III), and where, in the case of reacting a compound of formula (II) with an anthranilic acid derivative of formula (III) or in the case of reacting a carbamate of formula (V) with an anthranilic acid derivative of the formula (III), said reaction medium is an inert, aprotic solvent which is liquid under normal conditions, and wherein, in the case of reacting a compound of formula (II) with an alcohol of formula (IV), said reaction medium is said alcohol, a said inert, aprotic solvent which is liquid under normal conditions, or a combination thereof.

2. The process as claimed in clam 1, wherein $R^1$ to $R^9$ are hydrogen, halogen, $(C_1-C_6)$alkyl or $(C_1-C_6)$alkoxy.

3. The process as claimed in claim 1, wherein formula (I) is 3-(2,4-dichlorophenyl)-6-fluoro-2,4(1H,3H)-quinazolinedione.

4. The process as claimed in claim 1, wherein said catalyst is a compound or complex of a noble metal of the 8th subgroup.

5. The process as claimed in claim 1, wherein said catalyst is a noble metal of the 8th subgroup in metallic form on an inert support.

6. The process as claimed in claim 1, wherein the amount of said catalyst ranges from 0.001 to 10 mol %, relative to said compound of formula II.

7. The process as claimed in claim 1, wherein said ligand is an amine.

8. The process as claimed in claim 1, wherein, in said reaction between the compound of formula II and the compound of formula III, or in said reaction between the carbamate of formula V and an anthranilic acid derivative of the formula III, inert, said aprotic solvent is an aromatic hydrocarbon, an aliphatic hydrocarbon, a chlorinated aromatic compound, a chlorinated aliphatic compound, a heterocyclic compound, or a ketone.

9. The process as claimed in claim 1, wherein, in the reaction of a carbamate of the formula (V) with an anthranilic acid derivative of the formula (III), said base is an alkali metal or alkaline earth metal alkoxide, amide or hydroxide or a tetraalkyl-ammonium hydroxide.

10. The process as claimed in claim 1, wherein, in said reaction between the compound of formula II and the compound of formula III, or in said reaction of a carbamate of the formula (V) with an anthranilic acid derivative of the formula (III), said inert, aprotic solvent is toluene, xylene or dichlorobenzene.

11. The process as claimed in claim 9, wherein said alkali metal alkoxide is sodium methoxide.

12. The process as claimed in claim 10, wherein said reaction is the reaction between the compound of formula II and the compound of formula III.

13. The process as claimed in claim 10, wherein said reaction is the reaction between a carbamate of the formula (V) and an anthranilic acid derivative of the formula (III).

14. The process as claimed in claim 4, wherein said catalyst is a compound or complex of Pd, Ru, or Rh.

15. The process as claimed in claim 6, wherein the amount of said catalyst is 0.01 to 1 mol-%, relative to said compound of formula II.

* * * * *